(12) United States Patent
Gold

(10) Patent No.: US 7,297,691 B2
(45) Date of Patent: Nov. 20, 2007

(54) TREATMENT OF SLEEP DISORDERS WITH CHOLINESTERASE INHIBITORS

(75) Inventor: Michael Gold, Newtown, PA (US)

(73) Assignee: Janssen Pharmaceutica N.V. (BE)

( * ) Notice: Subject to any disclaimer, the term of this patent is extended or adjusted under 35 U.S.C. 154(b) by 293 days.

(21) Appl. No.: 10/915,821

(22) Filed: Aug. 11, 2004

(65) Prior Publication Data

US 2005/0038013 A1 Feb. 17, 2005

Related U.S. Application Data

(60) Provisional application No. 60/494,712, filed on Aug. 13, 2003.

(51) Int. Cl.
*A61K 31/55* (2006.01)
*A61K 31/343* (2006.01)
*A61K 31/222* (2006.01)

(52) U.S. Cl. ................ 514/215; 514/462; 514/468; 514/510

(58) Field of Classification Search ............... 514/215
See application file for complete search history.

(56) References Cited

U.S. PATENT DOCUMENTS 5,585,375 A 12/1996 Davis

FOREIGN PATENT DOCUMENTS

| EP | 0 515 302 | 11/1992 |
| WO | WO 97/22339 | 6/1997 |
| WO | WO00/25821 | * 5/2000 |
| WO | WO 01/30318 | 5/2001 |
| WO | WO 2004/034963 | 4/2004 |

OTHER PUBLICATIONS

2006 Chemical Abstracts Service Catalog, published by Chemical Abstracts Service, p. 52.*
Merck Manual of Diagnosis and Therapy, Seventeenth Edition, Beers et al., ed., (1999), Chapter 179, pp. 1409-1417.*
Timofeeva et al. "EEG Spectra, behavioral states, and motor activity in rats exposed to acetylcholinesterase inhibitor chlorpyrifos" Pharmacology, Biochemistry, and Behavior (2002) vol. 72, pp. 669-679.*
Banji et al. "Emergent Complications Following Donepezil Switchover to Galantamine in THree Cases of Dementia With Lewy Bodies" The Journal of Neuropsychiatry and Clinical Neurosciences (2005) vol. 17, No. 4, pp. 552-555.*
PCT International Search Report, dated Feb. 11, 2005, for PCT Int'l. Appln. No. PCT/US2004/026243.

* cited by examiner

*Primary Examiner*—Shaojia Anna Jiang
*Assistant Examiner*—Eric S Olson
(74) *Attorney, Agent, or Firm*—Mary Appollina

(57) ABSTRACT

The present invention is concerned with treatment of sleep disorders by administering a cholinesterase inhibitor, and in particular, by administering galantamine or a pharmaceutically acceptable salt thereof. Also in particular, cholinesterase inhibitors that are active at nicotinic receptors and that are selective for acetylcholinesterase over butylcholinesterase are used in treating sleep disorders.

10 Claims, No Drawings

TREATMENT OF SLEEP DISORDERS WITH CHOLINESTERASE INHIBITORS

CROSS-REFERENCE TO RELATED APPLICATIONS

This application claims priority from U.S. Provisional Application Ser. No. 60/494,712, filed Aug. 13, 2003, the contents of which are hereby incorporated by reference in their entirety.

STATEMENT REGARDING FEDERALLY SPONSORED RESEARCH OR DEVELOPMENT

The research and development of the invention described below was not federally sponsored.

BACKGROUND OF THE INVENTION

The present invention is concerned with treatment of sleep disorders by administering a cholinesterase inhibitor. In particular, cholinesterase inhibitors that are active at nicotinic receptors and that are selective for acetylcholinesterase over butylcholinesterase are used in treating sleep disorders.

Galantamine (structure immediately below), a tertiary alkaloid, has been isolated from the bulbs of the Caucasian snowdrops *Galanthus woronowi* (Proskurnina, N. F. and Yakoleva, A. P. 1952, Alkaloids of *Galanthus woronowi*. II. Isolation of a new alkaloid. (In Russian.) Zh. Obschchei Khim. (J. Gen. Chem.) 22, 1899-1902). It has also been isolated from the common snowdrop *Galanthus nivalis* (Boit, 1954).

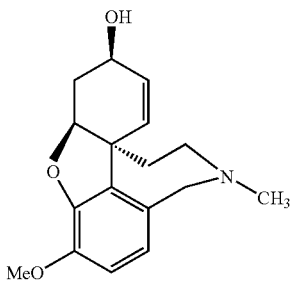

The chemical name of galantamine is [4aS-(4aα,6β,8aR*)]-4a,5,9,10 11,12-hexahydro-3-methoxy-11-methyl-6H-benzofuro[3a,3,2-ef][2]benzazepin-6-ol; both the base compound and its hydrobromide are laevorotatory. Galantamine is a well-known acetylcholinesterase inhibitor which is active at nicotinic receptor sites but not on muscarinic receptor sites. It is capable of passing the blood-brain barrier in humans, and presents no severe side effects in therapeutically effective dosages.

Acetylcholine is known to play a role in sleep and may have a more specific role in the regulation of REM sleep. (Shiromani et al. Annu. Rev Pharmacol Toxicol. 1987; 27:137-56) Furthermore, based on the dense cholinergic innervation of the basal forebrain, acetylcholine is thought to also play a role in sleep onset and maintenance (Donnet A, Encephale. 1993 May-June; 19(3):237-40.). Effects of acetylcholine on sleep can be seen under conditions of acetylcholine deficiency such as Alzheimer's disease or under conditions of cholinergic stimulation as after exposure to nicotine.

Dyssomnias are chronic disorders of sleep usually associated with excess sleepiness or complaints of insomnia. While some of these dyssomnias may be attributable to circadian disruptions (eg. jet-lag or shift work), others are due to instrinsic disorders related to the ability to fall asleep, remain asleep or arise from sleep without a precipitating event. Other forms of dyssomnias are related to external factors interfering with sleep (i.e. noise, hypnotic dependence, altitude) (International Classification of Sleep Disorders, 1990).

One of the cardinal features of restorative sleep is the need for the preservation of sleep architecture including adequate periods of REM sleep. Dyssomnias are often characterized by the disruption of normal sleep architecture and the loss of REM sleep. Cortical acetylcholine has been reported to be greatest during waking times and during REM sleep (Vazquez J, Am J Physiol. Regul. Integr. Comp. Physiol. 2001 February; 280(2):R598-601). This suggests that chronic sleep disorders characterized by disrupted sleep architecture including reduced and/or fragmented sleep may be amenable to treatment by drugs that increase CNS levels of acetylcholine.

Galantamine has been described for the treatment of sleep-disordered breathing such as snoring and apnea in WO-97/22339).

Galantamine has been used extensively as a curare reversal agent in anesthetic practice in Eastern bloc countries (cf. review by Paskow, 1986) and also experimentally in the West (cf. Bretagne and Valetta, 1965: Wislicki, 1967; Consanitis, 1971).

Galantamine has been marketed by Waldheim (Sanochemia Gruppe) as Nivalin™ in Germany and Austria since the 1970s for indications such as facial neuralgia.

The use of galantamine or an analogue or a pharmaceutically acceptable acid addition salt thereof for the preparation of a medicament for treating Alzheimer's Dementia (AD) and related dementias has been described in EP-0,236,684 (U.S. Pat. No. 4,663,318). This patent only has a generic disclosure of possible dosage forms of galantamine.

U.S. Pat. No. 5,585,375 claims galantamine for treatment of jet lag, when administered in an alertness-increasing amount.

The use of galantamine for treating alcoholism and the administration via a transdermal therapeutic system (TTS) or patch is disclosed in EP-0,449,247 and WO-94/16707. Similarly, the use of galantamine in the treatment of nicotine dependence using administration via a transdermal therapeutic system (TTS) or patch is disclosed in WO-94/16708. Treatment of nerve gas poisoning is disclosed in DE-4,342,174.

A number of applications by E. Snorrason disclose the use of galantamine, analogues thereof and pharmaceutically acceptable salts thereof for the preparation of medicaments for treating mania (U.S. Pat. No. 5,336,675), chronic fatigue syndrome (CFS) (EP-0,515,302; U.S. Pat. No. 5,312,817), the negative effects of benzodiazepine treatment (EP-0,515,301) and the treatment of schizophrenia (U.S. Pat. No. 5,633,238). In these applications and patents, e.g. in U.S. Pat. No. 5,312,817, a number of immediate release tablet formulations of galantamine hydrobromide are given.

WO-97/47304 discloses fast-dissolving or immediate release tablets of galantamine prepared by direct compression. These and other art-known immediate release tablets are administered twice (b.i.d.) or thrice (t.i.d.) daily with an interval of 8 hours. The plasma levels of the active ingredient typically raise sharply (early $T_{max}$ and relatively high $C_{max}$) and decline rapidly (deep trough after about 6 to 8 hours).

SUMMARY OF THE INVENTION

The present invention is directed to a method for the treatment of a sleep disorder, comprising administering, to a patient in need thereof, an effective amount of a pharmaceutically acceptable cholinesterase inhibitor or a prodrug therefor.

DETAILED DESCRIPTION OF THE INVENTION

As used herein, the term sleep disorder means dyssomnias. In particular, the method is directed to treatment of the dyssomnias classified and described in *ICSD—International classification of sleep disorders: Diagnostic and coding manual*. Diagnostic Classification Steering Committee, Thorpy M J, Chairman. Rochester, Minn.: American Sleep Disorders Association, 1990. In the present context, the term sleep disorder does not include sleep-disordered breathing such as snoring or sleep apnea, or sleep disorders associated with jet lag or alcoholism.

The following table lists sleep orders of particular interest in the present invention:

| Disorder | ICSD Classification |
| --- | --- |
| Intrinsic Sleep Disorders | |
| Psychophysiological Insomnia | 307.42-0 |
| Sleep State Misperception | 307.49-1 |
| Idiopathic Insomnia | 780.52-7 |
| Narcolepsy | 347 |
| Recurrent Hypersomnia | 780.54-2 |
| Idiopathic Hypersomnia | 780.54-7 |
| Posttraumatic Hypersomnia | 780.54-8 |
| Obstructive Sleep Apnea Syndrome | 780.53-0 |
| Central Sleep Apnea Syndrome | 780.51-0 |
| Central Alveolar Hypoventilation Syndrome | 780.51-1 |
| Periodic Limb Movement Disorder | 780.52-4 |
| Restles Legs Syndrome | 780.52-5 |
| Intrinsic Sleep Disorder NOS | 780.52-9 |
| Extrinsic Sleep Disorders | |
| Inadequate Sleep Hygiene | 307.41-1 |
| Environmental Sleep Disorder | 780.52-6 |
| Altitude Insomnia | 289.0 |
| Adjustment Sleep Disorder | 307.41-0 |
| Insufficient Sleep Syndrome | 307.49-4 |
| Limit-Setting Sleep Disorder | 307.42-4 |
| Sleep-Onset Association Disorder | 307.42-5 |
| Food Allergy Insomnia | 780.52-2 |
| Nocturnal Eating (Drinking) Syndrome | 780.52-8 |
| Hypnotic-Dependent Sleep Disorder | 780.52-0 |
| Stimulant-Dependent Sleep Disorder | 780.52-1 |
| Toxin-Induced Sleep Disorder | 780.54-6 |
| Extrinsic Sleep Disorder NOS | 780.52-9 |
| Circadian Rhythm Sleep Disorders | |
| Time Zone Change (Jet Lag) Syndrome | 307.45-0 |
| Shift Work Sleep Disorder | 307.45-1 |
| Irregular Sleep-Wake Pattern | 307.45-3 |
| Delayed Sleep Phase Syndrome | 780.55-0 |
| Advanced Sleep Phase Syndrome | 780.55-1 |
| Non-24-Hour Sleep-Wake Disorder | 780.55-2 |
| Circadian Rhythm Sleep Disorder NOS | 780.55-9 |

In particular, the present invention is directed to method for the treatment of a sleep disorder, comprising administering, to a patient in need thereof, an effective amount of a pharmaceutically acceptable cholinesterase inhibitor or a prodrug therefor wherein the sleep disorder is selected from the group consisting of insomnia, phase-lagging, In the present invention, particular cholinesterase inhibitors are selected from the group consisting of galantamine and galantamine derivatives, norgalantamine and norgalantamine derivatives, epigalantamine and epigalantamine derivatives, physostigmine, tacrine and tacrine analogues, fasciculin, metrifonate, heptyl-physostigmine, norpyridostigmine, norneostigmine, and huperzine, eptistigmine, or a prodrug therefor.

Of particular value for the present invention are cholinesterase inhibitors that are active substantially selectively at nicotinic receptor sites.

Also, of particular utility are acetylcholinesterase inhibitors that have an at least 10-fold selectivity for acetylcholinesterase as opposed to butyryl-cholinesterase. Particularly preferred are those acetylcholinesterase inhibitors that have an at least 20-fold selectivity for acetylcholinesterase as opposed to butyrylcholinesterase. Most preferred are acetylcholinesterase inhibitors that have an at least 40-fold selectivity for acetylcholinesterase as opposed to butyrylcholinesterase.

Also useful in the present invention are acetylcholinesterase inhibitors that upon administration in an amount of 10 mg to a healthy adult, result in inhibition of at least 40% of the acetylcholinesterase activity in erythrocytes from the adult and no substantial inhibition of butyrylcholinesterase therein. Preferably, the acetylcholinesterase inhibitor is one which, when administered in an amount of 10 mg to an adult, results in inhibition of at least 50% of the acetylcholinesterase activity in erythrocytes from the adult.

Cholinesterase inhibitors useful in the present invention are those capable of passing the blood-brain barrier in humans. Preferred are those that upon administration to a human increase the cortisol level in the human.

The cholinesterase inhibitor preferred in the present invention is galantamine or a salt, derivative or functional equivalent thereof.

Pharmaceutically acceptable cholinesterase inhibitors are, e.g., galantamine and galantamine derivatives, norgalantamine and norgalantamine derivatives, epigalantamine and galantamine, physostigmine, tacrine and tacrine analogues, fasciculin, metrifonate, heptyl-physostigmine, norpyridostigmine, norneostigmine, and huperzine or a prodrug therefor. Some of the cholinesterase inhibitors show certain undesirable properties, such as short half life, etc. In some cases, such deficiencies can be compensated for by modifying the compound into a prodrug for the active compound, in accordance with well-known principles for prodrug construction, such as introduction of hydrophilic groups to enhance the solubility of a compound in water (thus making it possible to formulate the compound as a an injection solution) an introduction of lipophilic groups such as ester groups to enhance the capability of the compound to pass the blood-brain barrier. The presently preferred cholinesterase inhibitor used according to the invention is galantamine. Galantamine is known as an acetylcholinesterase acting substantially only at nicotinic receptor sites, that is, having a high selectivity for acetylcholinesterase as opposed to butyrylcholinesterase. A more detailed discussion of galantamine and galantamine derivatives is given below:

Pharmacokinetic studies have recently been made by Thomsen, T. and H. Kewitz. (Selective Inhibition of Human Acetylcholinesterase by Galantamine in vitro and in vivo. Life Sciences, Vol 46, pp. 1553-1558 (1990), and, by the same authors, Galantamine Hydrobromide in a Long-Term Treatment of Alzheimer's Disease. Dementia 1990, 1:46-51).

It is believed that the excellent and surprising affect possessed by galantamine is due to its specific profile of properties, the most important of the known ones of which can be summarized as follows:

capability to pass the blood brain barrier in humans, a high selectivity for acetylcholinesterase as opposed to butyrylcholinesterase (about 50-fold when measured by the in vitro method by Thomsen et al., see below), a sufficient elimination half life to warrant duration of an effective concentration of at least 4 hours, probably at least 6 hours, a relatively low toxicity in therapeutic concentrations, capability of being effective in doses which are sufficiently low to keep peripheral side effects low.

Galantamine must be considered as being a very desirable drug for the treatment according to the invention: The elimination half life of galantamine hydrobromide is over four hours; it shows a practically complete renal elimination. A complete elimination of metabolites and galantamine takes place in 72 hours. Galantamine has been used in Eastern Block countries since around 1958 as an anticurare agent in anesthesiology, and a considerably number of patients have been treated with galantamine without any reported case of liver toxicity or serious side effects. Galantamine hydrobromide, being a tertiary amine and lipid soluble, is absorbed rapidly from the gut and transverses the blood brain barrier easily. The common side effects, other than the ones related to cholinergic crisis, are either nausea or vomiting, and a slight headache. However, these side effects are rare, especially when care is taken to start medication in low doses such as mentioned above.

The galantamine can suitably be administered orally in the form of an acid addition salt, e.g. the hydrobromide, but other administration forms are possible and realistic, such as is described below.

Because galantamine has substantially no effect on the activity at muscarinic receptor sites, as apparent from its high selectivity for acetylcholinesterase as opposed to butyrylcholinesterase, it will not give rise to the often severe side effects on the heart which are associated with cholinesterase inhibitors which have a low selectivity for acetylcholinesterase as opposed to butyrylcholinesterase. Galantamine has an in vitro selectivity for acetylcholinesterase opposed the effect on butyrylcholinesterase of 50 to 1, as reported by Thomsen, Life Sciences, Vol 46, pp. 1553-1558 (1990).

As indicated above, the amount of galantamine is preferably adjusted individually based upon observation of the effect of initially very low dosages. There is a considerable difference with respect to how sensitive individuals are to acetylcholinesterase inhibitors. Thus, the amount of galantamine is suitably adjusted by means of a regimen starting at low dosages, e.g. 1 mg, preferably at 5 mg, per day, but, if appropriate, even as low as 0.1 mg per day, if the dosage is well tolerated by the patient within the first two hours the dosages is increased to, e.g. 10 mg per dosage dosed 3 to 4 times per day or in some severe cases to 60 mg or more per day dosed over 3 or 4 times.

For treating sleep disorders, one may wish to attain effective plasma levels during the night, and lower levels during daytime. For the benefit of the patient and the caretakers, a pharmaceutical dosage form that has to be administered once daily only and yields effective plasma levels for eight hours (nighttime) to 16 hours (daytime) would be highly desirable.

Because cholinergic crisis, a life-threatening dose-dependant side effect of all kinds of acetylcholinesterase inhibitors, should, by all means, be avoided, it is recommended to start with the low dosages as mentioned above and furthermore not to exceed 150 mg per day and preferably not to exceed dosages above 60 mg per day, unless the patient shows a very low sensitivity to acetylcholinesterase inhibitor, in which case higher doses, such as 200 mg per day, could be used.

The treatment according to the invention should preferably be continued at least for two months, such as, e.g., three months, or until the syndrome has disappeared.

While galantamine has, indeed, given remarkable results, such as appears from the clinical cases given in the examples, it is justified to presume that other acetylcholinesterase inhibitors which are functional equivalents to galantamine with respect to its combination of high selectivity with respect to nicotinic receptor sites and capability of passing the blood brain barrier in humans in vivo, will also show a useful combination of effect against sleep disorders and acceptability in the clinic, although it cannot be ruled out that galantamine, galantamine salts and galantamine derivatives, due to the special conformation of the galantamine ring system, have specific properties which are decisive for the remarkable effect.

In accordance with the above, compounds which are functional equivalents of galantamine are defined herein as compounds which possess an at least 10-fold selectivity, preferably an at least 20-fold selectivity, more preferably an at least 40-fold selectivity, and most preferably an at least 50 fold selectivity, for acetylcholinesterase as opposed to butyrylcholinesterase, when measured by the in vitro method by Thomsen et al., see below, are capable of passing the blood brain barrier in humans in vivo.

As will be understood from the above definition, a compound can be subjected to well-defined and relatively short lasting tests (see below) to determine whether it fulfills criterion a) above. Then, the likelihood whether the compound will pass the blood brain barrier in humans in vivo (criterion b)) can be assessed in a model. One such model is a whole rat brain model in which rats are given the acetylcholine esterase in vivo and are then killed whereupon homogenate of the rat brain is examined with respect to the acetylcholinesterase activity; the result is then compared to the acetylcholinesterase activity in rat brains not treated with acetylcholinesterase inhibitors. Another rat model could be the measurement and comparison of acetylcholinesterase activity in cerebrospinal fluid in vivo in the same rat before and after treatment. If the compound fulfills criterion a), and its likelihood of passing the blood brain barrier has been established in one of the above-described rat brain models, it will be a candidate drug. An initial determination of toxicity is necessary in cases before any effect in humans can be assessed; such initial determination of toxicity can be performed by pharmacological tests in a manner known per se. After the pharmacological tests, the capability of the candidate drug of passing the blood brain barrier in humans in vivo can be determined by the method described below. If the candidate drug has been found to possess this capability, it can be passed to the testing proper. Optionally, the candidate drug can be subjected to additional short-lasting tests, such as the in vivo selectivity test described by Thomsen et al., and a test to determine whether it increases cortisol level in humans. Both of these tests give further indication of whether the candidate drug has a spectrum of properties equivalent to galantamine with respect to what must be presumed to be essential properties. Peripheral side effects will be assessable when the effect is tested clinically, which is acceptable from an experimental and ethical point of view, provided the toxicity has first been assessed by the above-mentioned pharmacological tests. With respect to the final assessment of the candidate drug's effect on sleep disorders, a rational and efficient design of the assessment will involve an initial test on one or a few patients and, provided the initial test is positive, the above-mentioned conclusive double blind test. Because of the well-defined and brief character of all of the tests, and especially the well-defined in vitro character of the initial screening, the test series for identifying useful functional equivalents of galantamine is a reasonable and not burdensome routine which is within the realm of the person skilled in the art.

Functional equivalents and derivatives of galantamine which are useful in the method of the invention will be employed in the same manner as stated herein for galantamine. Whenever quantities of such a functional equivalent or derivative are referred to herein, the quantities are given as the equipotent quantity of galantamine hydrobromide with respect to inhibition of acetylcholinesterase, that is, as the quantity of galantamine hydrobromide which results in the same inhibition of acetylcholine esterase in the above-mentioned in vitro test according to Thomsen et al as does the functional derivative or derivative.

The selectivity of the acetylcholinesterase inhibitor for acetylcholinesterase as opposed to butyrylcholinesterase can be determined by in vitro and in vivo tests as described by Thomsen and Kewitz in the above mentioned paper Selective Inhibition of Human Acetylcholinesterase by Galantamine in vitro and in vivo, Life Sciences, Vol 46, pp. 1553-1558 (1990), and T. Thomsen, H. Kewitz and O. Pleul, J. Clin. Chem. Clin. Biochem. 26 469-475 (1988). The in vitro test described by Thomsen and Kewitz in Life Sciences, Vol 46, pp 1553-1558 (1990) is the one referred to above in connection with criterion a) and whenever numeric (10-fold, 20-fold, 40-fold) reference to selectivity for acetylcholinesterase as opposed to butyrylcholinesterase is made in the claims. According to Thomsen and Kewitz, galantamine hydrobromide, when tested under the conditions described, shows a 50-fold selectivity; this selectivity value is taken as the "fixpoint" whenever in vitro selectivities are discussed herein and could be used, for the purpose of determining the selectivities for other cholinesterase inhibitors, as a calibration value which is the one to establish with galantamine hydrobromide in any repetition of the experiment described by Thomsen and Kewitz. Thus, with reference to this determination method, a preferred acetylcholinesterase inhibitor is one which in the in vitro method described has an at least 10-fold selectivity for acetylcholinesterase as opposed to butyrylcholinesterase, such as an at least 20-fold selectivity for acetylcholinesterase as opposed to butyrylcholinesterase, e.g. an at least 40-fold selectivity for acetylcholinesterase as opposed to butyrylcholinesterase.

A relatively easy commercially available selectivity test which can be used as a practical tool in the screening of candidate drugs is the test described in Example 1 herein.

The capability to pass the blood brain barrier in vivo in humans can be assessed by either by a test which could be called "Auditory brain stem response" or by a test which is based on the measurement of CRH, ACTH and cortisol. The rationale behind these tests, and the way they are performed, is explained in the following:

The auditory brain stem response test is based on the observation that manic-depressive (bipolar) patients are hypersensitive to cholinergic influences, one manifestation hereof being hypersensitivity to auditory signals as assessed by the increase of amplitude of auditory evoked potentials in the nuclei of the auditory system in the brain stem, i.e. on the "brain side" of the blood brain barrier. This hypersensitivity manifests itself in a lower amplitude than in normal humans when the person is not treated with a cholinergic agent such as acetylcholinesterase inhibitor; and a very significantly increase of the amplitude when the person has received a cholinergic agent, provided, of course, that the cholinergic agent is able to pass the blood brain barrier and thus enter the nuclei of the auditory system in the brain stem.

The other test based on the measurement of CRH (corticotropic-hormone releasing hormone released from the hypothalamus in the brain, and which releases both ACTH from the adenohypophysis and cortisol from the adrenal medulla) and ACTH (corticotropic hormone, which releases cortisol from the adrenal medulla) is carried out by measuring the CRH, ACTH and cortisol concentration in the blood in healthy persons before and after medication with acetylcholinesterase. If the concentration of all three hormone are increased after medication or at least CRH and cortisol are increased it is proven that the acetylcholinesterase has effect in the central nervous system, and since it is an in vivo experiment it is further proven that the acetylcholinesterase has passed the blood brain barrier.

As mentioned above, the selectivity of the acetylcholinesterase inhibitor can, as an additional characterization, optionally be expressed with reference to the in vivo determinations performed by Thomsen and Kewitz on galantamine and described in the above-mentioned paper Selective Inhibition of Human Acetylcholinesterase by Galantamine in vitro and in vivo, Life Sciences, Vol 46, pp. 1553-1558 (1990). With reference to this determination, a preferred acetylcholinesterase inhibitor is one which, upon administration in an amount of 10 mg to a healthy adult, results in inhibition of at least 40% of the acetylcholinesterase activity in erythrocytes from the adult within about 2-5 minutes and no substantial inhibition of butyrylcholinesterase therein, such as an acetylcholinesterase inhibitor which, when administered in an amount of 10 mg to a healthy adult, results in inhibition of at least 50% of the acetylcholinesterase activity in erythrocytes from the adult within about 2-5 minutes. For galantamine, Thomsen and Kewitz found 65% inhibition of acetylcholinesterase in the erythrocytes within 2 minutes after administration of 10 mg of galantamine i.v. in a healthy volunteer, whereas no inhibition of butyrylcholinesterase in plasma was seen. Also these determinations are referred to in claims herein and should, in connection with the evaluation of the corresponding selectivities of candidate drugs different from galantamine hydrobromide be considered the "calibration fixpoints" which will be established with galantamine hydrobromide in any repetition of this experiment.

As mentioned above, it is possible that galantamine, galantamine salts and galantamine derivatives, due to the special conformation of the galantamine ring system, have specific properties which are decisive for the remarkable effect established according to the present invention. Thus, according to one aspect of the invention, compounds which are contemplated to be valuable and useful in the treatment according to the invention are the compounds having the formula I (formula I also represents galantamine itself)

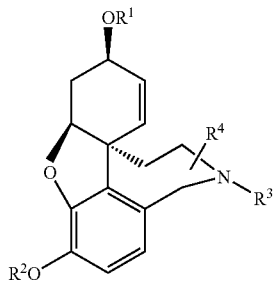

wherein $R^1$ and $R^2$ which may be the same or different each represents a hydrogen atom or an acyl group, such as a lower alkanoyl group, e.g. an acetyl group or a straight chained or branched alkyl group, e.g. methyl, ethyl, propyl, or isopropyl; $R^3$ is a straight or branched chain alkyl, alkenyl or alkaryl group which is optionally substituted by a halogen atom or a cycloalkyl, hydroxy, alkoxy, nitro, amino, aminoalkyl, acylamino, heteroaryl, heteroaryl-alkyl, aroyl, aroylalkyl or cyano group; and $R^4$ represents a hydrogen or halogen atom attached to at least one of the ring carbons of the tetracyclic skeleton, with the proviso that when $R^4$ is in a position neighboring the nitrogen atom, then $R^4$ is preferably different from halogen, and salts thereof, such as a hydrobromide, hydrochloride, methylsulphate or methiodide.

In the compounds of formula I, alkyl moieties preferably contain 1 to 8 carbon atoms, halogen atoms are preferably fluorine, chlorine, or bromine, especially fluorine or chlorine, aryl moieties are preferably phenyl, cycloalkyl groups are preferably 3- to 7-membered rings, especially cyclopropyl or cyclobutyl, and heteroaryl moieties are preferably 5- to 8-membered rings, e.g., thienyl, furyl, pyridyl, pyrrolyl, or pyrizanyl.

Among the compounds of the formula I are those described in EP-A-236684. The compounds of formula I may be prepared according to conventional techniques, including those described in EP-A-236684.

A broader range of compounds which, from the point of view of structural similarity with galantamine, are contemplated to be valuable compounds useful in the method of the invention are galantamine derivatives of the general formula II

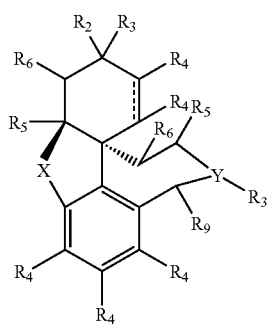

wherein the broken line ( - - - ) represents an optionally present double bond in the position shown, $R_1$ and $R_2$ are each selected independently from the group consisting of hydrogen, hydroxyl, amino or alkylamino, cyano, sulfhydryl, alkoxy of 1-6 carbon atoms, alkylthio, aryloxy, arylthio, $R_5$-substituted aryloxy, $R_5$-substituted arylthio, aralkoxy, an aliphatic or aryl carbamyl group wherein the aliphatic or aryl moiety may be $R_5$ substituted or unsubstituted, aralkylthio, $R_5$-substituted aralkoxy, $R_5$-substituted aralkylthio, aryloxymethyl, $R_5$-substituted aryloxymethyl, alkanoyloxy, hydroxy-substituted alkanoyloxy, benzoyloxy, $R_5$-substituted benzoyloxy, aryloxycarbonyl and $R_5$-substituted aryloxycarbonyl, $R_1$ may also be alkyl of up to 14 carbon atoms, or hydroxymethyl, $R_2$ may also be carboxymethyl, provided that at least one of $R_1$ and $R_2$ is hydroxy, amino or alkylamino unless $R_8$ is hydroxymethyl, $R_3$ is hydrogen, straight or branched chain alkyl of 1-6 carbon atoms, cycloalkylmethyl, phenyl, $R_5$-substituted phenyl, alkylphenyl, $R_5$-substituted alkylphenyl, heterocyclyl selected from .alpha.- or .beta.-furyl, .alpha.- or .beta.-thienyl, thenyl, pyridyl, pyrazinyl, and pyrimidyl, alkyl-heterocyclyl or R'-substituted heterocyclyl, where R' is alkyl or alkoxy, each $R_4$ is independently selected from hydrogen, hydroxyl, sulfhydryl, alkyl, aryl, aralkyl, alkoxy, mercaptoalkyl, aryloxy, thiaryloxy, alkaryloxy, mercaptoalkaryl, nitro, amino, N-alkylamino, N-arylamino, N-alkarylamino, fluoro, chloro, bromo, iodo, and trifluoromethyl, $R_5$ is selected from the same groups as $R_4$, $R_6$ is hydrogen, halo, trifluoromethyl or alkyl of 1 to 4 carbon atoms, with the proviso that when R.sup.6 is in position 7 or 9, it is preferably not halo, $R_7$ is selected from the same groups as $R_4$ or may be hydroxyalkyl of 1-2 carbon atoms, $R_8$ is hydrogen or hydroxymethyl, $R_9$ is hydrogen or alkyl of 1 to 6 carbon atoms, or when $R_2$ is hydroxyl, $R_9$ may be a moiety of formula I wherein $R_9$ is hydrogen and $R_2$ is a linking bond; or $R_2$ and $R_9$ may jointly form semicarbazone, X is oxygen or $NR_5$, Y is nitrogen or phosphorus, and methylenedioxy derivatives thereof with the proviso that when X is O, $R_3$ is not methyl when $R_1$ is methoxy, $R_2$ is hydroxy, and all $R_4$ are hydrogen, or a pharmaceutically acceptable salt thereof.

Examples of subclasses and specific compounds of the formula II are given in U.S. Pat. No. 6,150,354 (incorporated herein by reference as if fully set forth), which also discloses methods for preparing the compounds II.

Galantamine, galantamine salts, galantamine derivatives and galantamine functional equivalents, when suited therefor, may be administered orally at a dosage of e.g. 5-150 mg per day, such as 10-60 mg per day, e.g. 10-50 mg, such as 10-40 mg, per day, the dosage being adapted to the patient and the patient's response. As mentioned above, the treatment should often be started with a low dosage and then increased until the suitable dosage has been established. The dosage of galantamine functional equivalents or galantamine derivatives is expressed as the equipotent amount of galantamine hydrobromide, the reference basis being the capability of inhibiting acetylcholinesterase in the Thomsen et al. in vitro test mentioned above. Preferably, an oral once-daily dosage of galantamine (such as that disclosed in U.S. patent application Ser. No. 09/868,991 filed Jul. 26, 2001 and incorporated herein by reference as if fully set forth) is used in the present invention.

Examples of parenteral administration ranges are 0.1-1000 mg per day such as 5-1000 mg per day, e.g. 10-500 mg per day, including 50-300 mg per day; lower dosages are often preferred, such as 10-50 mg per day, e.g. 10-30 mg per day.

For the oral administration, galantamine or a galantamine salt or derivative or a functional equivalent may be formulated, for example, as an aqueous suspension or a solution in aqueous ethanol or as a solid composition such as a tablet or capsule. Suspensions or solutions for oral administration are typically of a concentration of 1-50 mg/ml, more commonly 5-40 mg/ml, for example, 10-40 mg/ml, typically 20-30 mg/ml of galantamine. Divided doses into the range 0.5-5 mg/kg body weight per day are useful, in some situations divided doses in the range of 0.1-3 mg/kg body weight per day may also prove useful. Examples of dosages are up to 2000 mg per day, such as 0.1-2000 mg per day, or 5-2000 mg per day. Other ranges that should be mentioned are 100-600 mg per day or 10-500 mg per day, such as 10-50 or 10-30 mg per day. Typically, one might administer a dosage of 20-100 mg per day to a patient of a body weight of 40-100 kg, although in appropriate cases such dosages may prove useful for patients having a body weight outside this range. However, in other instances dosages of 50-300 mg per day to a patient of a body weight of 40-100 kg may be also be very useful. In other cases, dosages as low as 10 mg and as high as 200 mg may be appropriate for persons in this body weight range.

The cholinesterase inhibitors useful in the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201-217; J. Pharm. Sci., 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope administering prodrugs of cholinesterase inhibitors. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Galantamine and its acid addition salts form crystals. They are generally only sparingly soluble in water at room temperature; therefore, injectable compositions are normally in the form of an aqueous suspension. If necessary, pharmaceutically-acceptable suspension aids may be employed. Typically, such a suspension will be employed at a concentration of 0.1-50 mg/ml, such as 1-50 mg/ml, more commonly 5-40 mg/ml, for example, 5-30 mg/ml or 10-40 mg/ml, such as 10-30 mg/ml, especially 20-30 mg/ml of galantamine. As mentioned above, typical dosage rates when administering galantamine by injection are the range 0.01-20 mg per day depending upon the patient. For example, divided doses in the range 0.5-5 mg/kg body weight per day may prove useful. Typically, one might administer a dosage of 5-50 mg per day to a patient of a body weight of 40-100 kg, although in appropriate cases such dosages may prove useful for patients having a body weight outside this range. In other cases, dosages as low as 5 mg and as high as 200 mg per day may be appropriate for persons in this body weight range.

Galantamine and its pharmaceutically acceptable acid addition salts, and its derivatives and functional equivalents, when suited therefor, may be administered by subcutaneous, intravenous or intramuscular injection.

The parenteral dosage rate of galantamine can also be expressed by reference to the body weight of the patient; in this case, a normal dosage rate will often be 0.1 to 4 mg/kg body weight. Depot compositions will often deliver a dosage rate of 0.01 to 5.0 mg/kg per day.

In preparing tablets or capsules, standard tablet or capsule-making techniques may be employed. If desired, a pharmaceutically acceptable carrier such as starch or lactose may be used in preparing galantamine or galantamine equivalent tablets. Capsules may be prepared using soft gelatin as the encapsulating agent. If desired, such capsules may be in the form of sustained release capsules wherein the main capsule contains microcapsules of galantamine or functional equivalents thereof which release the contents over a period of several hours thereby maintaining a constant level of galantamine or its functional equivalent in the patient's blood.

The following specific formulations may find use according to the invention:

Tablets or capsules containing 0.1, 1, 2, 5, 10 and 25 mg galantamine hydrobromide or functional equivalent to be taken four times a day, or a sustained-release preparation delivering an equivalent daily dose.

Liquid formulation for oral administration available in 5 mg/ml and 25 mg/ml concentration.

Other interesting administration forms of galantamine and functional equivalents are suppositories, a slow-release plaster, and other depot compositions.

All of the above-mentioned administration forms are prepared in manners known per se.

Although galantamine must be considered as having a high degree of safety, there have been certain side effects in a few of the patients treated. These have been slight nausea in about 30% of the cases (the nausea, however, disappearing after about one week of treatment), vomiting and dizziness in 5-10% of the patients (also disappearing after about one week of treatment in most cases), and more severe side effects in 4-6% of the patients. These more severe side effects must be considered acceptable in view of the effect of the drug; however, in patients who are suspected of developing arrhythmia, it should be considered to administer, e.g., atropine in combination with the treatment according to the invention.

The administration forms for the cholinesterase inhibitors, galantamine, the galantamine salts and the galantamine derivatives may be orally and perenterally. The administration being dependent on the patient's age and weight, and on the daily life of the patient as well as the severity of the disease.

Parenteral administration may comprise suitable injection, e.g. intravenous, intramuscular, subcutaneous, as well as transdermal or rectally administration or implantation of e.g. suitable delivery devices, such as a intrathetical device.

Formulations for parenteral use may be a solution or suspension, a plaster for transdermal application, or a suppository.

EXAMPLE 1

Test for Cholinesterase Activity in Blood Samples

Method

SIGMA DIAGNOSTICS® CHOLINESTERASE (PTC) kit, available from Sigma Diagnostics, can be used for determining the activity and selectivity of cholinesterase inhibitors. In the following, it is illustrated how the kit is used for the determination of the activity and selectivity of Nivalin (Galantamine hydrobromide).

Reactions involved in the cholinesterase assay are as follows:

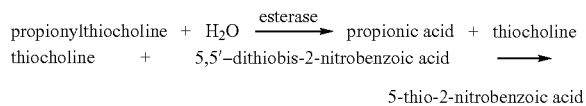

5-thio-2-nitrobenzoic acid is assessed by measuring the absorbance at 405 nm. The rate of change in absorbance at 405 nm is directly proportional to cholinesterase activity.

The activity of erythrocyte cholinesterase may be calculated on the basis of the measurement of butyrylcholinesterase (pseudocholinesterase) in serum and cholinesterase in hemolyzed whole blood (hemolysate), both measured simultaneously by the method described above, and evaluated according to the hematocrit value according to the formula $HchE = (EchE \times Hct^*) + (PchE \times (1-Hct^*))$ Therefore, $EchE = (HchE - (PchE \times (1-Hct^*)))/Hct^*$.

Hematocrit value expressed as decimal equivalent (i.e. 25%=0.25)

In the above formulae, EChE is erythrocyte cholinesterase activity, PChE is plasma cholinesterase activity, HChE is hemolysate cholinesterase activity, and Hct is hematocrit value of the sample.

Another way of assessing the cholinesterase activity is to measure the plasma cholinesterase and the cholinesterase in purified hemolyzed erythrocytes. By doing this, the values are obtained directly.

Blood samples from 3 patients are tested with the Sigma test. The tests are carried out with samples where no Nivalin was added and with samples where 1.25 µg/ml Nivalin and 2.5 µg/ml were added in vitro. The results are shown below in table 1.1.

TABLE 1.1

| Nivalin added µg/ml | Hemolysate ChE activity | Serum ChE activity |
| --- | --- | --- |
| 0 | 1.00 | 1.00 |
| 1.25 | 0.96 | 0.98 |
| 2.50 | 0.86 | 0.97 |

The results show a significant reduction of the hemolysate cholinesterase activity with increased concentration of galantamine hydrobromide, whereas the data for the serum activity do not show any statistically significant change as a response to the addition of the galantamine hydrobromide, which is an indication of a high selectivity of the galantamine hydrobromide with respect to acetylcholinesterase as opposed to butyrylcholinesterase. Selectivity for acetylcholinesterase in erythrocytes opposed to butyrylcholinesterase is contemplated to reflect the selectivity for acetylcholinesterase at nicotinic receptor sites opposed to the acetylcholinesterase at muscarinic receptor sites.

This test may be used as a screening for candidate cholinesterase inhibitors with respect to their selectivity.

EXAMPLE 2

Galantamine Treatment of Sleep Disorders

A prospective, double-blind, placebo-controlled, parallel group study of the efficacy of an acetylcholinesterase inhibitor on polysomnographic (PSG) parameters in a group of idiopathic chronic insomniacs is performed. These subjects are taught sleep hygiene during a placebo-run in period. PSG parameters are obtained at baseline, then the subjects are randomized and treated for a period of several weeks with 4-24 mg of galantamine or another acetylcholinesterase inhibitor after which PSG parameters are measured again. In addition, patient diaries related to sleep quality are recorded. The active treatment demonstrates increased sleep efficiency, and an increased or solidified amount of REM sleep and that the subjects feel that their sleep quality is improved.

What is claimed is:

1. A method for the treatment of idiopathic chronic insomnia comprising administering, to a patient in need thereof, an effective amount of a cholinesterase inhibitor selected from the group consisting of galantamine, a galantamine salt or a galantamine derivative of the formula I

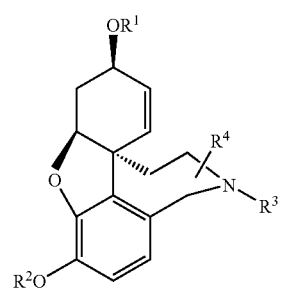

wherein $R^1$ and $R^2$ which may be the same or different each represents a hydrogen atom or an acyl group, such as a lower alkanoyl group, e.g. an acetyl group or a straight-chained or branched alkyl group, e.g. methyl, ethyl, propyl, or isopropyl;

R³ is a straight or branched chain alkyl, alkenyl or alkaryl group which is optionally substituted by a halogen atom or a cycloalkyl, hydroxy, alkoxy, nitro, amino, aminoalkyl, acylamino, heteroaryl, heteroaryl-alkyl, aroyl, aroylalkyl or cyano group; and R⁴ represents a hydrogen or halogen atom attached to at least one of the ring carbons of the tetracyclic skeleton, with the proviso that when R₄ is in a position neighboring the nitrogen atom, then R₄ is different from halogen, and salts thereof, such as a hydrobromide, hydrochloride, methylsulphate or methiodide;

or the formula II

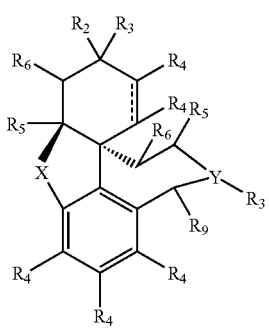

wherein the broken line ( - - - ) represents an optionally present double bond in the position shown, R₁ and R₂ are each selected independently from the group consisting of hydrogen, hydroxyl, amino or alkylamino, cyano, sulfhydryl, alkoxy of 1-6 carbon atoms, alkylthio, aryloxy, arylthio, R₅-substituted aryloxy, R₅-substituted arylthio, aralkoxy, an aliphatic or aryl carbamyl group wherein the aliphatic or aryl moiety may be R₅ substituted or unsubstituted, aralkylthio, R₅-substituted aralkoxy, R₅-substituted aralkylthio, aryloxymethyl, R₅-substituted aryloxymethyl, alkanoyloxy, hydroxy-substituted alkanoyloxy, benzoyloxy, R₅-substituted benzoyloxy, aryloxycarbonyl and R₅-substituted aryloxycarbonyl, R₁ may also be alkyl of up to 14 carbon atoms, or hydroxymethyl, R₂ may also be carboxymethyl, provided that at least one of R₁ and R₂ is hydroxy, amino or alkylamino unless R₈ is hydroxymethyl, R₃ is hydrogen, straight or branched chain alkyl of 1-6 carbon atoms, cycloalkylmethyl, phenyl, R₅-substituted phenyl, alkylphenyl, R₅-substituted alkylphenyl, heterocyclyl selected from .alpha.- or .beta.-furyl, .alpha.- or .beta.-thienyl or thenyl, pyridyl, pyrazinyl, and pyrimidyl, alkyl-heterocyclyl or R'-substituted heterocyclyl, where R' is alkyl or alkoxy, each R₄ is independently selected from hydrogen, hydroxyl, sulfhydryl, alkyl, aryl, aralkyl, alkoxy, mercaptoalkyl, aryloxy, thiaryloxy, alkaryloxy, mercaptoalkaryl, nitro, amino, N-alkylamino, N-arylamino, N-alkarylamino, fluoro, chloro, bromo, iodo, and trifluoromethyl, R₅ is selected from the same groups as R₄, R₆ is hydrogen, halo, trifluoromethyl or alkyl of 1 to 4 carbon atoms with the proviso that when R₆ is in position 7 or 9, it is not halo, R₈ is hydrogen or hydroxymethyl, R₉ is hydrogen or alkyl of 1 to 6 carbon atoms, or when R₂ is hydroxyl, R₉ may be a moiety of formula I wherein R₉ is hydrogen and R₂ is a linking bond; or R₂ and R₉ may jointly form semicarbazone, X is oxygen or NR₅, Y is nitrogen or phosphorus, and methylendioxy derivatives thereof with the proviso that when X is O, R₃ is not methyl when R₁ is methoxy, R₂ is hydroxy, and all R₄ are hydrogen;

and pharmaceutically acceptable salts thereof.

2. A method according to claim 1, wherein the galantamine salt is galantamine hydrobromide.

3. A method according to claim 1, wherein the galantamine derivative is one which is able to cross the blood brain barrier in humans.

4. A method according to claim 1, wherein the cholinesterase inhibitor is administered in the form of a pharmaceutical composition which is a tablet, a capsule, a sustained release capsule comprising micro capsules of the active ingredient, a solution or suspension, a plaster for transdermal application, or a suppository.

5. A method according to claim 1, in which the cholinesterase inhibitor is administered perenterally at a dosage which is equipotent with 0.1-1,000 mg of galantamine hydrobromide per day, such as 5-1,000 mg of galantamine hydrobromide.

6. A method according to claim 5, in which the cholinesterase inhibitor is administered in a dosage which is equipotent with to 10-500 mg galantamine hydrobromide per day, such as 50-300 mg per day.

7. A method according to claim 5, in which the cholinesterase inhibitor is administered in a dosage which is equipotent with 10-50, in particular 10-30, mg galantamine hydrobromide per day.

8. A method according to claim 1, in which the cholinesterase inhibitor is administered orally in a dosage which is equipotent with 5-2000 mg galantamine hydrobromide per day.

9. A method according to claim 8, in which the cholinesterase inhibitor is administered at a dosage which is equipotent with 10-500 mg galantamine hydrobromide per day.

10. A method according to claim 9, in which the cholinesterase inhibitor is administered at a dosage which is equipotent with 10-50 mg, such as 10-30 mg, of galantamine hydrobromide per day.

* * * * *